US006584260B2

(12) United States Patent
Arie et al.

(10) Patent No.: US 6,584,260 B2
(45) Date of Patent: Jun. 24, 2003

(54) ELECTRO-OPTICAL DEVICE AND A WAVELENGTH SELECTION METHOD UTILIZING THE SAME

(75) Inventors: Ady Arie, Herzeliya (IL); Amir Burstein, Tel Aviv (IL)

(73) Assignee: ZettaLight Dynamic Communications Israel, Moshav Bet Halevy (IL)

( * ) Notice: Subject to any disclaimer, the term of this patent is extended or adjusted under 35 U.S.C. 154(b) by 10 days.

(21) Appl. No.: 09/735,057

(22) Filed: Dec. 11, 2000

(65) Prior Publication Data

US 2002/0101648 A1 Aug. 1, 2002

(51) Int. Cl.[7] .................................................. G02B 6/00
(52) U.S. Cl. ......................... 385/122; 385/15; 385/16; 385/1; 385/2; 385/3; 385/129; 385/130; 385/131; 385/37; 385/10; 385/11
(58) Field of Search ......................... 385/1, 2, 3, 11, 385/129, 130, 131, 132, 37, 122, 10

(56) References Cited

U.S. PATENT DOCUMENTS

| 5,193,023 A | | 3/1993 | Yamada et al. ............. 359/345 |
| 5,581,642 A | | 12/1996 | Deacon et al. ............... 385/15 |
| 5,586,206 A | | 12/1996 | Brinkman et al. ............. 385/2 |
| 5,630,004 A | | 5/1997 | Deacon et al. ............. 385/129 |
| 5,703,710 A | | 12/1997 | Brinkman et al. ........... 359/283 |
| 5,715,092 A | * | 2/1998 | Gupta et al. ................ 359/566 |
| 5,732,177 A | | 3/1998 | Deacon et al. ............. 385/122 |
| 5,734,772 A | * | 3/1998 | Gopalan et al. ............ 385/122 |
| 5,756,263 A | * | 5/1998 | Gupta et al. ................ 430/317 |
| 5,781,670 A | | 7/1998 | Deacon et al. ............. 385/10 |
| 5,786,926 A | | 7/1998 | Yamada ....................... 359/250 |
| 5,852,688 A | | 12/1998 | Brinkman et al. ............ 385/16 |
| 5,875,053 A | * | 2/1999 | Webjorn et al. ......... 204/157.15 |
| 5,943,465 A | * | 8/1999 | Kawaguchi et al. ......... 385/122 |
| 6,074,594 A | | 6/2000 | Byer et al. .................. 264/406 |
| 6,353,495 B1 | * | 3/2002 | Mizuuchi et al. ........... 359/326 |

FOREIGN PATENT DOCUMENTS

| EP | 0 664 474 | 7/1995 | ............... 385/16 X |
| JP | 2000098432 | 7/2000 | ............... 385/16 X |

OTHER PUBLICATIONS

M. Rochette, M. Guy, S. LaRochelle, J. Lauzon, and F. Trépanier, "Gain Equalization of EDFA's with Bragg Gratings", IEEE Photonics Technology Letters, vol. 11, No. 5, May 1999, pp. 536–538.

S. E. Harris, R.W. Wallace, "Acousto–Optic Tunable Filter", Journal of the Optical Society of America, vol. 59, No. 6, Jun. 1969, pp. 744–747.

(List continued on next page.)

Primary Examiner—Brian Healy
(74) Attorney, Agent, or Firm—Greer, Burns & Crain, Ltd.

(57) ABSTRACT

A method and an electro-optical device are presented for affecting the propagation of input light impinging on the device. The electro-optical device is composed of at least one domain-patterned ferroelectric crystal structure with inverted domains, and an electrodes' arrangement on the surface of the at least one structure connected to a voltage source. When the input light is appropriately directed onto the electro-optical device, and voltage is appropriately applied to the electrodes, this causes at least one of the following effects: deflecting a light component of a predetermined wavelengths contained in the input light from the direction of propagation of the input light so as to direct this light component in a reflection output direction, while allowing the other light components to propagate in the direction of propagation of the input light; changing the phase of the input light in a wavelength-dependent manner; and separately controlling the wavelength-dependent transmission and dispersion for different polarizations of light.

18 Claims, 6 Drawing Sheets

OTHER PUBLICATIONS

J.M. Hammer, "Digital Electro–Optic Grating Deflector and Modulator", Applied Physics Letters, vol. 18, No. 4, Feb. 1971, pp. 147–149.

L.E. Myers, R.C. Eckardt, M.M. Fejer, R.L. Byer, "Quasi–Phase–Matched Optical Parametric Oscillators in Bulk Periodically Poled LiNbO3", J. Opt. Soc. Am. B, vol. 12, No. 11, Nov. 1995, pp. 2102–16.

M. Yamada, M. Saitoh, H. Ooki, "Electric–Field Induced Cylindrical Lens, Switching and Deflection Devices Composed of the Inverted Domains in LiNbO3 Crystals", Applied Physics Letters, vol. 69, No. 24, Dec. 1996, pp. 3659–3661.

H. Kogelnik, "Coupled Wage Theory for Thick Hologram Gratings", Bell System Technical Journal, vol. 48, No. 9, Nov. 1969, pp. 2909–2947.

H. Gnew uch, C.N. Pannell, G.W. Ross, P.G.R. Smith, H. Geiger, "Nanosecond Response of Bragg Deflectors in Periodically Poled LiNbO3", IEEE Photonics Technology Letters, vol. 10, No. 12, Dec. 1998, pp. 1730–1732.

"A Temperature–Dependent Dispersion Equation for Congruently Grown Lithium Niobate", Optical and Quantum Electronics Short Communication, vol. 16, 1984, pp. 373–374.

P. Yeh, "Optical Waves in Layered Media", John Wiley & Sons, 1988, pp. 185–192.

* cited by examiner

ELECTRO-OPTICAL DEVICE AND A WAVELENGTH SELECTION METHOD UTILIZING THE SAME

FIELD OF THE INVENTION

This invention relates to an electro-optical device, particularly for filtering, wavelength-selective switching, wavelength-selective modulation, temporal pulse shaping, and controllable dispersion

BACKGROUND OF THE INVENTION

Filters and other wavelength selective elements are widely used as passive devices relying, for example, on thin-film interference or on fixed diffraction gratings.

One kind of active device, such as a tunable or electrically-controllable filter, relies on interference. These include two-beam interferometers (e.g., Michelson, Mach-Zehnder) and multiple-beam interferometers (e.g., Fabry-Perot), where the optical path length can be varied by various mechanisms, e.g., by using thermal, piezoelectric or electro-optic effects. Filters utilizing these interferometers are usually sensitive to environmental perturbations, since variations of a fraction of the wavelength in the optical path length may substantially alter the filter performance.

Other types of tunable or electrically-controllable filters rely on diffraction, e.g., Bragg diffraction. In this type of filters, extremely wide free-spectral range, as well as good spectral resolution, can be attained, and these filters are usually less sensitive to environmental perturbations than the interference-based filters. The most widely used filters of this kind are acousto-optic tunable filters, disclosed, for example in the following publication: "*Acousto optic tunable filter*", S. E. Harris and R. W. Wallace, Journal of the Optical Society of America 59, 744 (1968). However, the acousto-optic tunable filters require continuous injection of an acoustic wave into the material, and therefore consume relatively high electrical power. In addition, they shift the frequency of light, and are inherently slow (typical switching speed exceeding 500 nsec), which makes them impractical for packet switching in high-speed optical communication systems.

Some of the above problems can be solved by using an electro-optic tunable filter, where an electro-optic grating is formed by placing inter-digital electrodes on the surface of an electro-optic material. In this case, the electric field has a suitable shape for filtering in the material only in a small region close to the electrodes. This device is mainly used with optical waveguides, but not with freely propagating beams in bulk crystals. Electro-optic modulators in bulk could be used only with relatively wide period of the electrodes, e.g., 300 $\mu$m as disclosed in the following publication: "*Digital electro-optic grating deflector and modulator*", J. M. Hammer, Applied Physics Letters 18, 147–149 (1971). In this case, high spectral resolution cannot be achieved.

In the last few years, techniques of patterning the domain structure of ferroelectric crystals such as $LiNbO_3$, $KTiOPO_4$ and $LiTaO_3$ have been developed, and disclosed for example in the following publications: "*Quasi-phase-matched optical parametric oscillator in bulk periodically poled $LiNbO_3$*", L. E. Myers et al., J. Opt. Soc. Am B 2102–2116 (1995), and U.S. Pat. Nos. 5,193,023 and 6,074,594. According to these techniques, a permanent grating of the non-linear susceptibility can be written into the material, for example, by applying once a very high field through patterned electrodes. The grating period can be in the range of several microns. The ferroelectric materials that can be domain-patterned are commercially available in large quantities, and the method of patterning the domains is well established.

The reversal of the ferroelectic domains also reverses the sign of the electro-optic coefficient. This is disclosed, for example in the following publication: "*Electric-field induced cylindrical lens, switching and deflection devices composed of the inverted domains in $LiNbO_3$ crystals*", M. Yamada, M. Saitoh and H. Ooki, Applied Physics Letters 69, 3659–3661 (1996). Hence, applying an external electric field will create a refractive index pattern inside the material, since the same electric field that increases the refractive index in one domain will reduce the refractive index in the inverted domain. Hence, the refractive index pattern depends also on the domain pattern of the ferroelectric crystal, and not only on the external electric field. Electro-optic devices based on domain-patterned ferroelectric crystals were used for deflection, modulation and beam focussing, as disclosed, for example, in U.S. Pat. No. 5,786,926.

SUMMARY OF THE INVENTION

There is accordingly a need in the art to facilitate the tuning and controlling of the propagation of an optical signal by providing a novel electro-optical device and method of the kind utilizing the electro-optical effect in domain-patterned ferroelectric crystals.

The device of the present invention can operate as an electronically-controlled optical filter and other wavelength selective optical elements, such as a switch, modulator, dispersion compensator and polarization mode dispersion compensator, having wide free spectral range, high spectral resolution, low power consumption and fast switching speed. Optical filters and other wavelength-selective optical elements according to the invention can be used with freely propagating beams. Generally speaking, the device according to the present invention enables wavelength selection, and utilizes a method for affecting the phase of light impinging on the device in a wavelength-dependent manner.

Electrically-controlled optical filters and other wavelength-selective optical elements are very important for optical communication systems. Dense wavelength division multiplexed (DWDM) optical communication systems require devices that can selectively manipulate different, closely spaced optical channels. One example of such an optical device that is often used in wavelength-routed systems is an add/drop multiplexer (ADM), where data on one or more optical channels are dropped at a certain node, while new data is added on the same wavelengths.

The conventional ADMs are mainly passive devices. It is desired to make an ADM as an active (or re-configurable) device that enables to dynamically change the dropped and added channels, in order to adjust the number of channels to the varying traffic volume in different locations in the system. More advanced systems should be able to switch data packets at predetermined wavelengths, and require a switching time in the nanosecond range.

The optical device according to the invention relies on a structure made of a ferroelectric crystal such as $LiNbO_3$, $KTiOPO_4$, $LiTaO_3$, $MgOLiNbO_3$, $KTiOAsO_4$, $RbTiOAsO_4$, $KNbO_3$, with patterned domains, and electrodes on the surface of the structure. In these domain-patterned crystals and in contrary to the standard mono-domain crystals, the refractive index pattern in the material is determined not only by the electrodes on the surface, but by the domain pattern as well. For a given domain pattern in the structure, by directing a light component of a predetermined wavelength onto the structure at a certain angle of incidence satisfying the Bragg condition for this predetermined wavelength, and applying voltage to the electrodes, this light component can be appropriately deflected to propagate with a certain direction. This can be used for selecting the light component of the predetermined wavelength from input light containing a plurality of wavelengths including this predetermined wavelength.

There is thus provided according to one aspect of the present invention, a method affecting the propagation of input light, the method comprising the steps of:
(i) passing the input light through an electro-optical device composed of at least one domain-patterned ferroelectric crystal structure with inverted domains, and an electrodes' arrangement on the surface of the at least one structure connected to a voltage source; and
(ii) applying voltage to the electrodes, thereby causing at least one of the following: deflecting a light component of a predetermined wavelengths contained in the input light from the direction of propagation of the input light so as to direct said light component in a reflection output direction, while allowing the other light components to propagate in said direction of propagation of the input light; changing the phase of the input light in a wavelength-dependent manner; and separately controlling the wavelength-dependent transmission and dispersion for light components of different polarizations contained in the input light.

According to another aspect of the present invention, there is provided a method of selecting a light component of a predetermined wavelength from input light formed of a plurality of light components of different wavelengths including said predetermined wavelength, the method comprising the steps of:
directing the input light onto an electro-optical device at an angle satisfying the Bragg condition for said predetermined wavelength, wherein said electro-optical device is composed of a domain-patterned ferroelectric crystal structure with inverted domains, and an electrodes' arrangement on the surface of said structure connected to a voltage source; and
applying voltage to the electrodes, thereby deflecting the light component of said predetermined wavelengths from the direction of propagation of the input light direction to propagate in a reflection output direction, while allowing the other light components to propagate in said direction of propagation of the input light.

According to yet another aspect of the present invention, there is provided an electro-optical device comprising:
(a) a domain-patterned ferroelectric crystal structure with inverted domains;
(b) an electrodes' arrangement on the surface of said structure connectable to a voltage source to selectively apply voltage to each of the electrodes;
(c) at least one input port for directing at least one input beam onto the structure; and
(d) a control unit operable for selectively affecting at least one of the following: an angle of incidence of the input beam onto the structure, the shape of the input beam, propagation of light components of different polarizations contained in the input beam, and a voltage applied to the electrodes.

The device can operate as a controllable filter, the filter transmission being controllable by varying at least one of the following: structure of the inverted domains, shape of the electrodes, voltage applied to each of the electrodes, the shape of the input beam, and an angle of incidence of the input beam.

The device can operate as a wavelength selective switch. The wavelength selection can be performed by directing the input beams onto said structure at different angles of incidence, thereby providing output beams ensuing from the structure with different angles of propagation, the angle of propagation of the output beam depending on the wavelength of the input beam. The device can thus operate as an electrically-controlled add, drop or add/drop switch. The device can also operate as a wavelength selective modulator.

By using the device according to the invention in an optical communication system, for example of the kind utilizing an optical amplifier with wavelength dependent gain, equalizing of the amplified power as a function of wavelength can be achieved. The device can be used for voltage controlled pulse shaping. In particular, this can be used to correct the dispersion accumulated in optical or fiber-optic communication system, and can handle changing levels of dispersion by appropriate selection of patterned domain structure and applied voltage through the electrodes.

The device can be used for wavelength dependent packet-switching in optical communication systems. By providing polarization beam splitters and retarders in the input port and at an output of the device, the wavelength-dependent transmission and dispersion can be separately controlled for different polarizations of light. For example, it can be used to correct polarization dependent loss and polarization mode dispersion in optical systems.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

Figure 1:
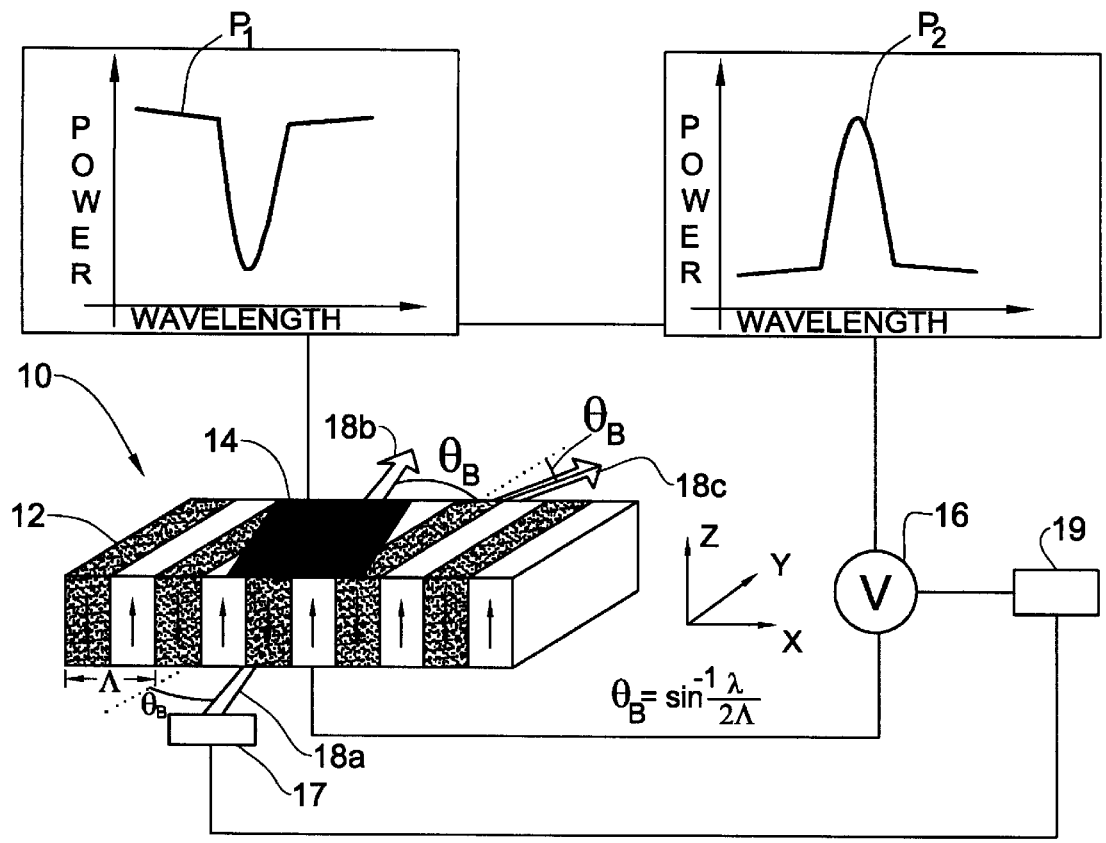
FIG. 1 is a schematic illustration of a wavelength selective switch according to the invention.

Referring to FIG. 1, there is illustrated an electro-optical device 10 according to the invention. The device comprises a domain-patterned ferroelectric crystal structure 12 with an electrodes' arrangement 14 on the surface of the structure 12 connectable to a voltage source 16, an input port 17 directing an input light beam 18a onto the structure, and a control unit 19 connected to the voltage source 16 and to the input port 17. In the present example, the domains are shown as periodically inverted. It should, however, be noted hat the periodicity of the inverted domains is not necessarily for the purposes of the present invention and a periodic gratings may be used as well. As shown, the reversal of the ferroelectric domains reverses the sign of the electro-optic coefficient.

The input light beam 18a is directed onto the crystal structure 12 at an angle satisfying the Bragg condition (at first or higher order). When no voltage is applied to the electrodes 14, all the power 18b comes out through a transmission output port. Applying voltage through the electrodes 14 can switch certain wavelengths from this direction to the reflection output direction 18c. Light at wavelengths that are far enough from the Bragg wavelength will not be switched, regardless of the applied voltage. Two graphs $P_1$ and $P_2$ show the typical transmission as a function of wavelength for, respectively, the transmitted and Bragg-reflected output beams 18b and 18c.

The device 10 can operate as a wavelength selective optical switch or controllable filter. The process of controlling the filter transmission can be based on one or more of the following parameters: structure of the domains, the shape of the electrodes, the applied voltage in each electrode, the beam shape and the beam angle of incidence. To use the device 10 as a wavelength selective switch, input beams with various angles of incidence are switched into output beams with different angles of propagation, where the switching depends on the wavelength of each input beam.

The application of a homogenous external electric field through the plane electrodes 14 to the periodically-poled crystal structure 12 (with a period $\Lambda$) creates a grating with the strength proportional to the strength of the electric field. The grating thickness is the entire thickness of the crystal, and therefore the beams do not have to be confined to a small region near the surface, thereby enabling the use of freely propagating beams. This is fundamentally different than applying voltage through periodic electrodes on a mono-domain crystal where the beams must be confined to a small region near the surface. This also allows using short gratings, and the state of the art for the period $\Lambda$, which is currently below 10 μm. Short grating periods enable to obtain high spectral resolution.

A lightwave component of wavelength $\lambda_B$ contained in the input beam 18a and entering the device 10 at an angle of incidence $(+\theta_{B,m})$ will be diffracted at an angle $(-\theta_{B,m})$, provided the Bragg condition is satisfied:

$$\sin(\theta_{B,m}) = \frac{m\lambda}{2n\Lambda}$$

wherein n is the refractive index of the structure 12, and m is the diffraction order.

Light at sufficiently different wavelengths will not satisfy the Bragg condition, and therefore will not be affected by the external field. This feature is particularly attractive to DWDM optical communication systems, since it allows switching in or out a single channel, without altering all the other channels. The amount of light that is Bragg diffracted at every wavelength is controlled by an electric field, and the rise time is in the nanosecond regime.

As known ("Coupled wave theory for thick hologram grating", H. Kogelnik, Bell System Technical Journal 48, 2909–2947 (1969), the spectral resolution is given by:

$$\Delta\lambda = \frac{\lambda \cdot \Lambda}{L \cdot m \cdot \tan(\theta_B)}$$

Assuming $\lambda$=1.55 μm, $\Lambda$=6.5 μm, L=25 mm (crystal length) and m=3, the wavelength bandwidth becomes equal to 0.8 nm, which is the channel spacing in DWDM systems. Narrower resolution of 0.4 nm cam also be achieved by using a 50 mm long crystal.

The specific filtered wavelength can be controlled by rotating the crystal 12 to change the angle of incidence or by changing the temperature of the device. Another option is to put several different gratings on the same chip with different electrodes and selecting the required channel by applying electric field to the appropriate electrode.

Yet another application is to use several different gratings (thus having different spectral response) to perform dynamic equalization of the power between different channels. Many elements in the optical link, including Erbium doped fiber amplifiers (EDFAs), optical cross-connects, et. have a non-uniform spectral response. While passive filters are currently used to correct the response, as optical systems become more complex, active equalization will be required, and it can be performed using the technique of the present invention.

Switches, attenuators and modulators based on the concept of the present invention can be very fast. It is known that a pulse rise time of 1.2 nanosecond can be achieved in an electro-optic Bragg deflector ("Nanosecond response of Bragg deflectors in periodically poled $LiNbO_3$," H. Gnewuch et al., IEEE Photonics Technology Letters 10, 1730–1732 (1998)). It is important to note that in the device according to the present invention, since it is based on electrostatic effect, the power consumption is minimal.

For the purposes of experiment, the inventors have constructed and tested a 12-mm long, 0.5-mm thick, periodically-poled $LiNbO_3$-based device 10 with a poling period of 29.6 μm. Wavelength and angle bandwidths have been measured up to the $5^{th}$ diffraction order, and wavelength bandwidth of 15 nm was obtained, in good agreement with the theoretical modeling.

Figure 2:
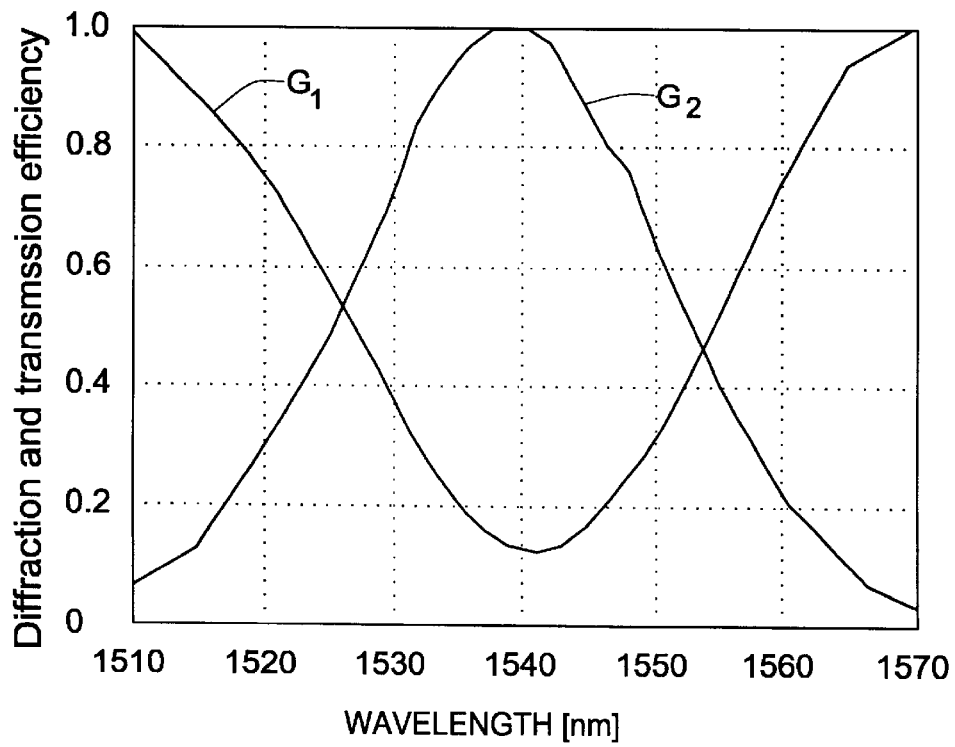
FIG. 2 illustrates the wavelength dependence of transmitted and diffracted beams in the device of FIG. 1.
Figure 3:
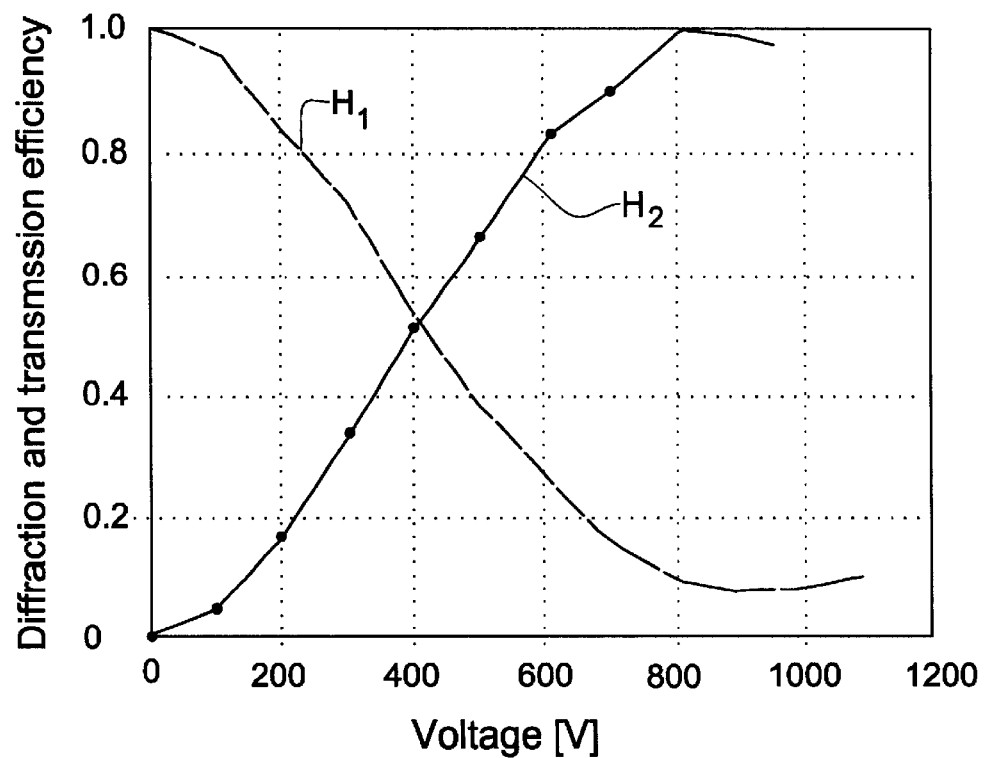
FIG. 3 illustrates the voltage dependence of transmitted and diffracted beams in the device of FIG. 1.
Figure 4:
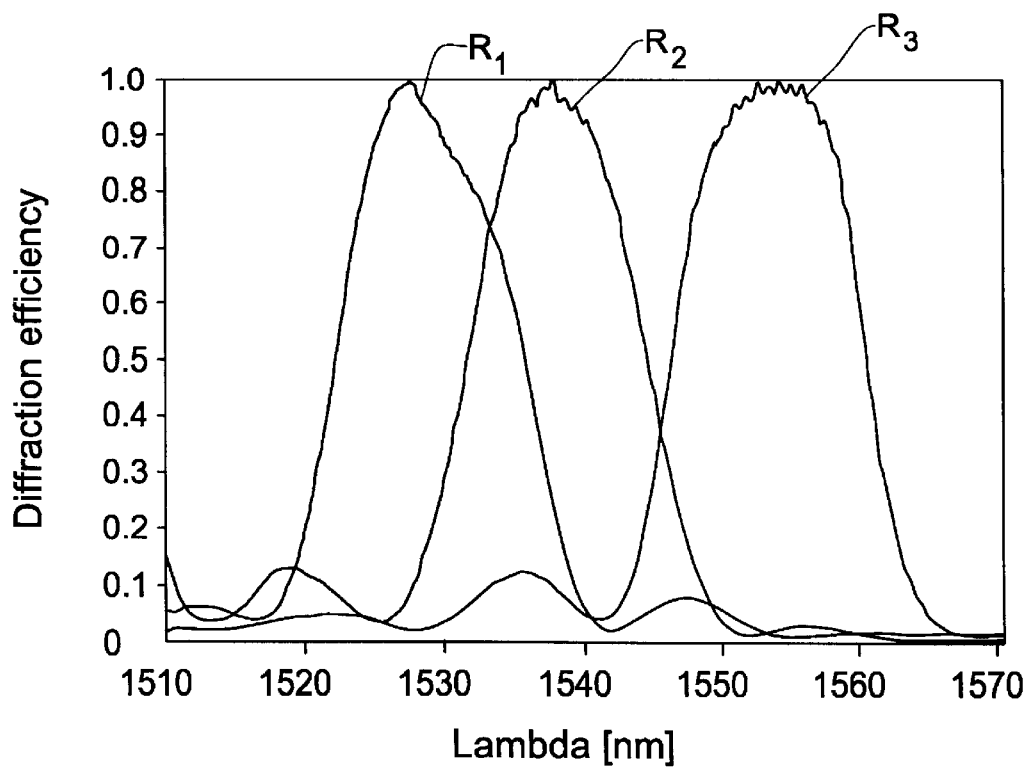
FIG. 4 illustrates the effect of an input angle on wavelength dependence of the switch of FIG. 1 for three different input angles.

FIGS. 2, 3 and 4 illustrate the measurement results in the form of diffraction and transmission efficiency as a function of wavelength, applied voltage and angle of incidence of the input beam. More specifically, in FIG. 2, the diffraction and transmission efficiency as a function of wavelength is shown for the $3^{rd}$ order of diffraction. Here, graphs $G_1$ and $G_2$ correspond to the wavelength dependence of the transmitted and diffracted beams, respectively. In FIG. 3, graphs $H_1$ and $H_2$ correspond to the voltage dependency of the zero-order transmitted beam and $3^{rd}$ order diffracted beam, respectively. In FIG. 4, three graphs $R_1$, $R_2$ and $R_3$ are shown corresponding, respectively, to the angular dependence of the switch for three different angles of incidence of the input beam: $\theta_1$=12.06 milli radian; $\theta_1$=12.14 milli radian; and $\theta_1$=12.29 milli radian. In these experiments, the device was also switched with an electric sine-wave at 7 MHz (rise time of 22 nanoseconds).

To improve the spectral resolution of the device, the present invention enables to use high order diffraction grating. In the previous experiments utilizing the Bragg effect, as disclosed in the above-indicated publications, the first is diffraction order was employed. However, for high spectral resolution, it is better to use higher orders of diffraction. The spectral resolution of the device is proportional to $1/m^2$, where m is the diffraction order. This requires entering at an appropriate incidence angle $\theta_{B,m}$ as described above.

It was found by the inventors that diffraction efficiency of more than 90% can be reached for example at third order (FIG. 2), and at the same time the spectral resolution is improved by a factor of 9 with respect to the first order diffraction efficiency.

Preferably, an elliptically-shaped beam is used to improve the spectral resolution of the optical device. This is associated with the following:

The domain patterning process currently requires ferroelectric crystals with thickness in the range of 0.5–1 mm. There is also motivation to use a relatively thin crystal in order to lower the voltage requirements of the electrodes, since the electro-optic effect is proportional to the electric field, given by V/d, where V is the voltage applied to the electrode and d is the crystal thickness. Usually a circular beam is used, but in this case the spectral resolution of the device is reduced as well. For example, assuming d=0.5 mm, a reasonable choice for Gaussian beam radius size $\omega_0$ that will have low clipping is as follows:

$$\omega_0 = \frac{d}{3} \approx 170 \mu m$$

In this case, a diffraction angle is determined as:

$$\Delta\theta_{diffraction} = \frac{\lambda}{\pi\omega_0}$$

Assuming for example that the wavelength $\lambda$ is 1.55 $\mu$m, the diffraction angle becomes equal to 2.9 milli Radian.

Assuming a periodically patterned nonlinear crystal with a period $\Lambda$, the angular acceptance bandwidth is related to the spectral resolution trough the ratio:

$$\frac{\Delta\theta_{Bragg}}{\theta_{Bragg}} = \frac{\Delta\lambda}{\lambda}$$

However, if the angular acceptance bandwidth becomes smaller than the diffraction angle, the spectral resolution of the device will be limited by the angular spread of the beam. For example, using the values given above of $\Lambda$=6.5 $\mu$m and m=3 in the periodically-poled LiNbO$_3$, the spectral resolution near 1.55 $\mu$m with a circular beam will be 26.8 nm instead of 0.8 nm (33 times wider). This problem can be solved by using an elliptic beam, where the size of the beam in the orthogonal direction (X-direction) is no longer limited by the thickness of the device. To achieve the spectral resolution of 0.8 nm, the radius of the beam should be larger than 5.7 mm in the X-direction, but can remain 0.17 mm in the Z-direction. It should be noted that even if thicker domain-patterned structures can be realized, it is still advantageous to use thin devices and elliptic beams in order to reduce the voltage requirements.

Figure 5:
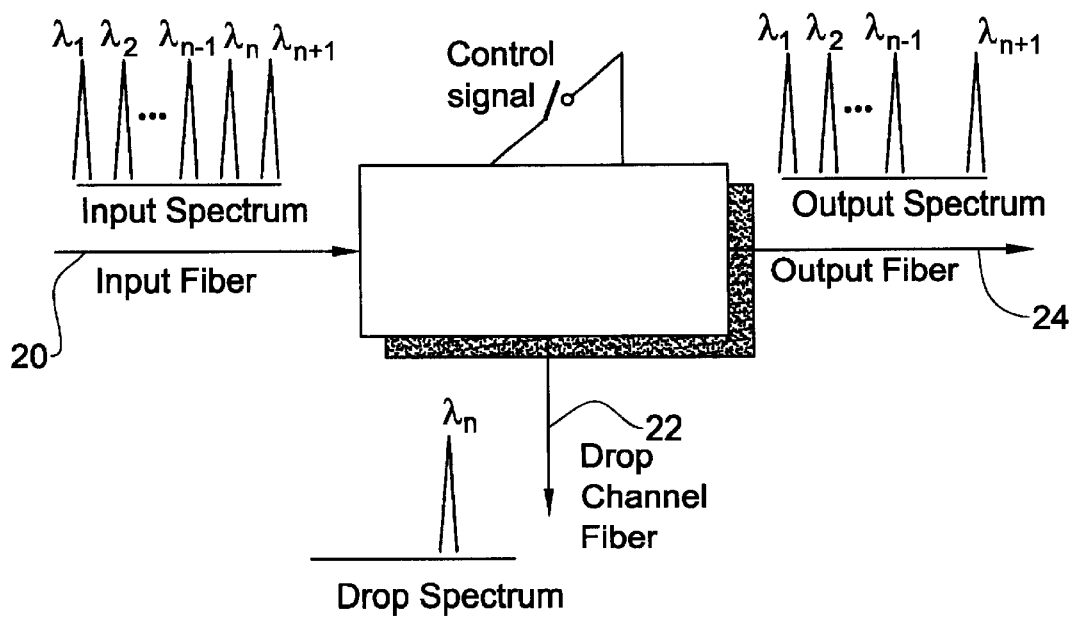
FIG. 5 schematically illustrates a drop switch utilizing the device of FIG. 1.
Figure 6:
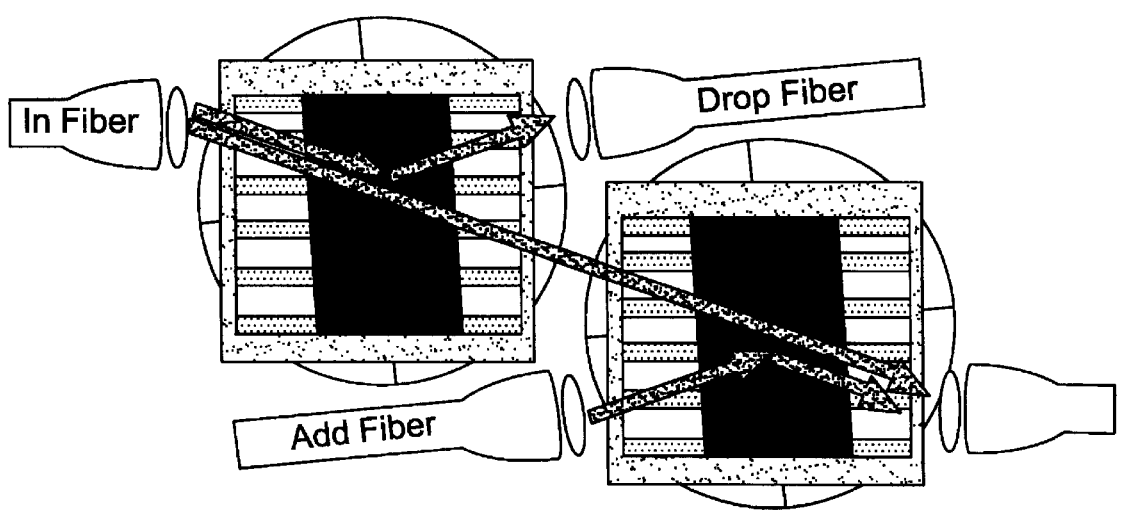
FIG. 6 schematically illustrates an add/drop switch utilizing the device of FIG. 1.

Referring to FIG. 5, there is illustrated how the device 10 can be used as an electrically-controlled drop switch. As shown, input light propagating through an input fiber 20 contains a plurality of light components of different wavelengths. When voltage is applied through the electrode(s) (not shown), either all input light or part thereof is switched to a "drop" port to enter a drop channel fiber 22, provided the wavelength of this light satisfies a certain condition, otherwise it comes out through a main output port to enter an output fiber 24. When no voltage is applied, all the light comes out through the main output port. In a similar manner, although not specifically shown, an add-switch can be realized, where the wavelength selective switching is performed on the input beams. Finally, add/drop switching can also be realized in this way, as shown in FIG. 6.

It should be understood that the device 10 can be used for wavelength selective modulation in the following manner: when a modulating voltage is applied to an input beam, only wavelength satisfying a certain condition will be modulated. The applied voltage will not affect light signals at other wavelengths.

Figure 7:
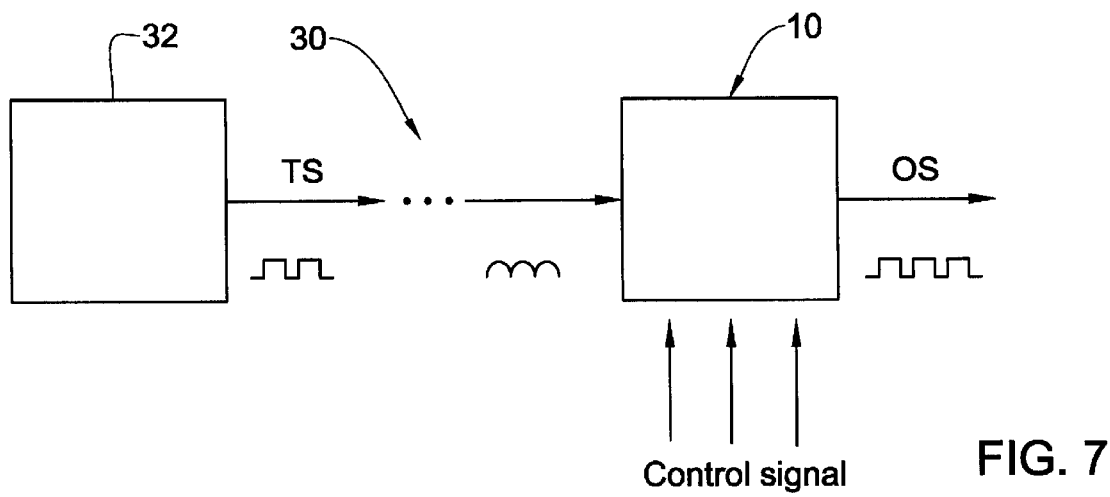
FIG. 7 illustrates how the device according to the present invention can be used for dispersion compensation in an optical communication system.

The device 10 can be used for producing voltage-controlled dispersion and pulse shaping, for example aimed at correcting the dispersion accumulated in an optical or fiber-optic communication system, and can handle changing levels of dispersion by the appropriate selection of the patterned domain structure and applied voltage through electrodes. This is illustrated in FIG. 7, showing a part of an optical communication system 30 composed of a transmitted unit 32 and the device 10 accommodated in the optical path of a transmitted signal TS. As shown, the transmitted signal TS, when reaching the device 10, is typically broadened owing to dispersion. By applying appropriate voltage to the electrodes (via transmission of control signals to the voltage source), the shape of the transmitted signal is reconstructed to produce an output signal OS. The filter transfer function H($\omega$) is in general a complex function of the angular velocity $\omega$ of the signal, the phase response of the transfer function being given by the arctan of the ratio between the imaginary and real part of the function H($\omega$). The group delay $\tau(\omega)$ and the dispersion D($\lambda$) are given by:

$$\tau(\omega) = -\frac{d\phi(\omega)}{d(\omega)}$$

$$D(\lambda) = \frac{d\tau}{d\lambda}$$

Without the application of external voltage, the dispersion of the device 10 (FIG. 1) is that of the bulk material (crystal structure 12). Denoting the device length by L and the refraction index by n, the phase response is: $\omega nL/c$. For example, for a 1 cm long LiNbO$_3$ crystal structure, at a wavelength of 1550 nm the dispersion is −0.08 ps/nm. This is calculated using the known Sellmeir equation ("A temperature-dependent dispersion equation for congruently grown LiNbO$_3$", Optical & Quantum Electronics, Vol. 16, p. 373). Assuming that the crystal is periodically-poled so that the Bragg diffracted light is reflected with an angle of 180° with respect to the input light when an electric filed is applied to the device, the domain structure should have a period of $\lambda/2n\Lambda \approx 0.362$ $\mu$m. In this case, the reflection coefficient and, in particular, its phase response can be calculated analytically (e.g., as disclosed in "Optical Waves in Layered Media", P. Yeh, New York, Wiley, 1988). The delay and dispersion can then be calculated from the derivatives of the phase response, as shown above.

Figure 8:
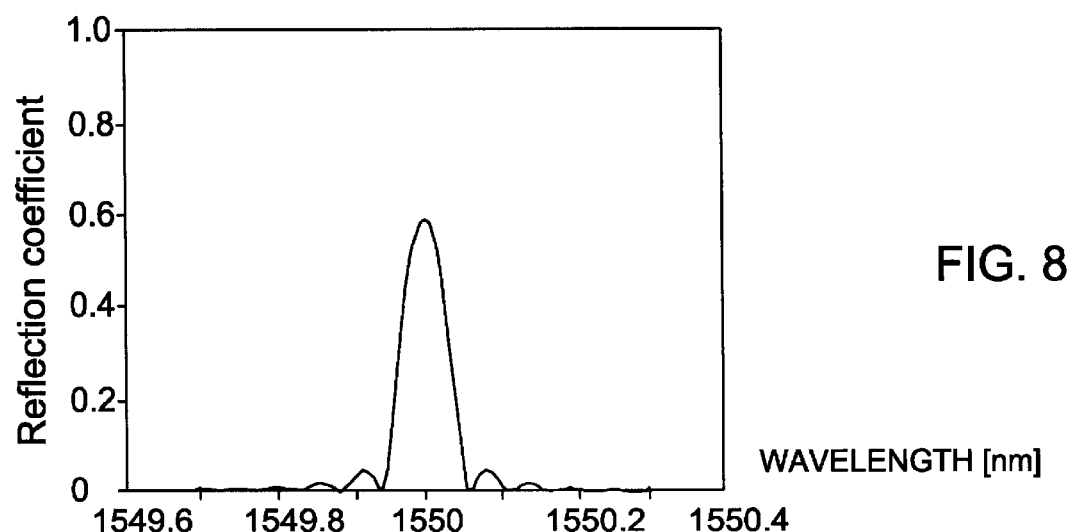
FIGS. 8 and 9 illustrate the intensity and dispersion response of a filter using the device of FIG. 1.
Figure 9:
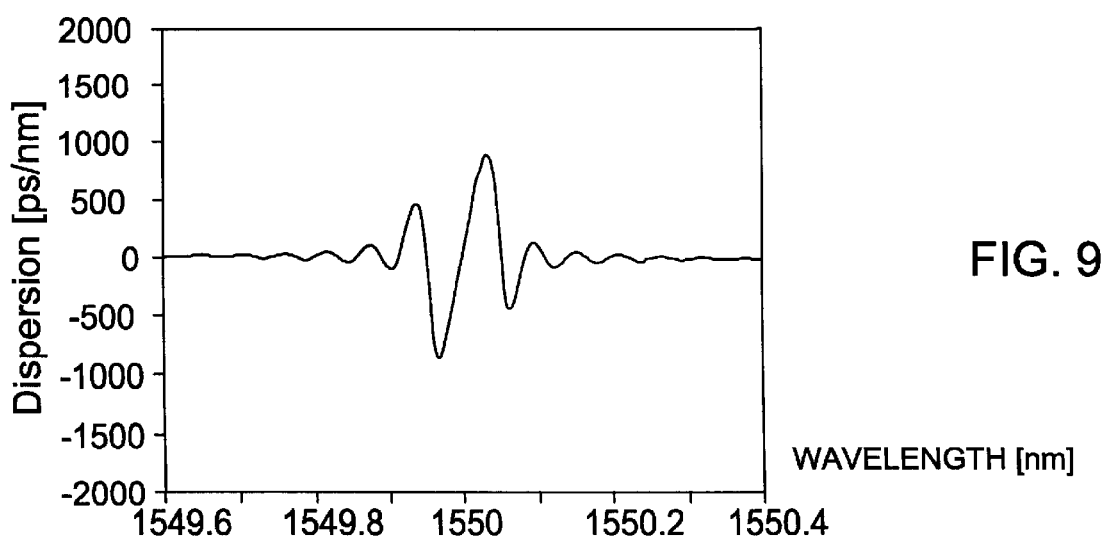

Turning now to FIGS. 8 and 9, there are illustrated the calculated intensity reflection profile of a domain-patterned LiNbO$_3$ (FIG. 8) and the calculated dispersion profile of this structure (FIG. 9) for $\Delta$n of $5\times10^{-5}$. As shown, the dispersion can reach 880 ps/nm, which is 4 orders of magnitude higher than the dispersion without the electric field. Hence, the group delay and the dispersion can be varied by applying an electric field to a domain-patterned crystal. This can be used to control the temporal shape of light pulses in general, and in particular to dynamically compensate the dispersion accumulated in optical communication systems.

It should be understood, although not specifically shown, that since the device according to the invention provides for a switching time in the nanosecond range, the device can be used for wavelength dependent packet-switching in optical communication systems. To this end, an electronic device is used of the kind capable of reading the header of a data packet to enable the selection of appropriate voltage to be applied to the electrodes so as to either switch the data packet or let it pass unaltered.

Figure 10:
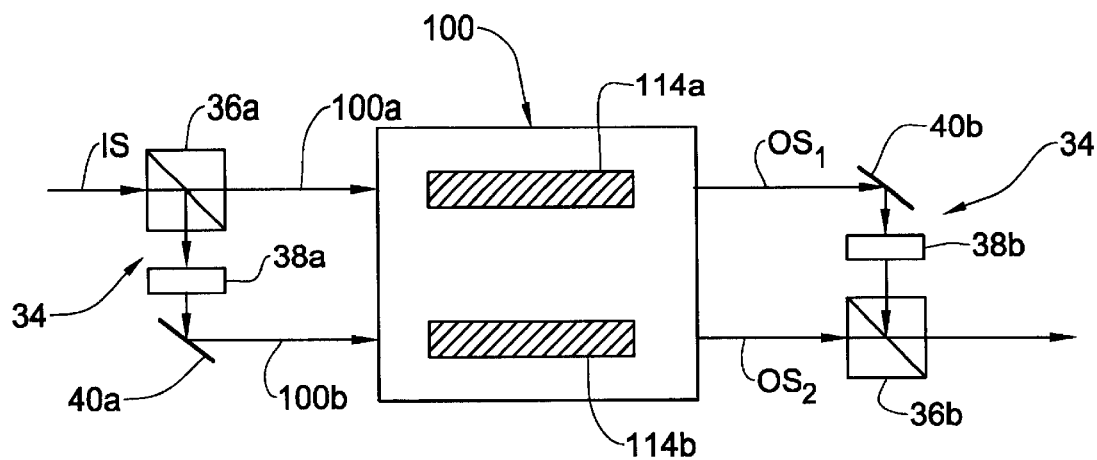
FIG. 10 illustrates how the device according to the present invention can be used for separate control of the wavelength-dependent transmission and dispersion for different polarizations of light.

Referring to FIG. 10, there is illustrated how the device according to the present invention can be used for separate control of the wavelength-dependent transmission and dispersion for different polarizations of light. A device 100 is of the kind providing two channels for light propagation 100a and 100b, each channel being constructed as in the above described device 10. This can be implemented by fabricating two domain-patterned ferroelectric crystal structures (12 in FIG. 1) in a spaced-apart parallel relationship in a common crystal and providing electrodes' arrangements 114a and 114b on the surfaces of the two structures. Input and output ports are provided with light directing means, generally at 34, composed of polarization beam splitters and retarders accommodated upstream and downstream of the device 100, so as to be in the optical paths of an input signal IS and two output signals $OS_1$, and $OS_2$.

Thus, the input arbitrary polarized beam IS passes through the polarizing beam splitter 36a, which reflects one light component of one polarization towards the channel 100a, and transmits the other light component of the other polarization towards a half-waveplate 38a and a mirror 40a, which reflects this light component towards the channel 100b. The output beam $OS_1$ ensuing from the channel 100a is reflected by a mirror 40b to pass through a half-waveplate 38b and a polarizing beam splitter 36b, and the output beam $OS_2$ ensuing from the channel 100b passes through the beam splitter 36b. This can, for example, be used to provide polarization independent operation of an optical system, to correct polarization dependent loss and to compensate polarization mode dispersion in optical systems.

Figure 11:
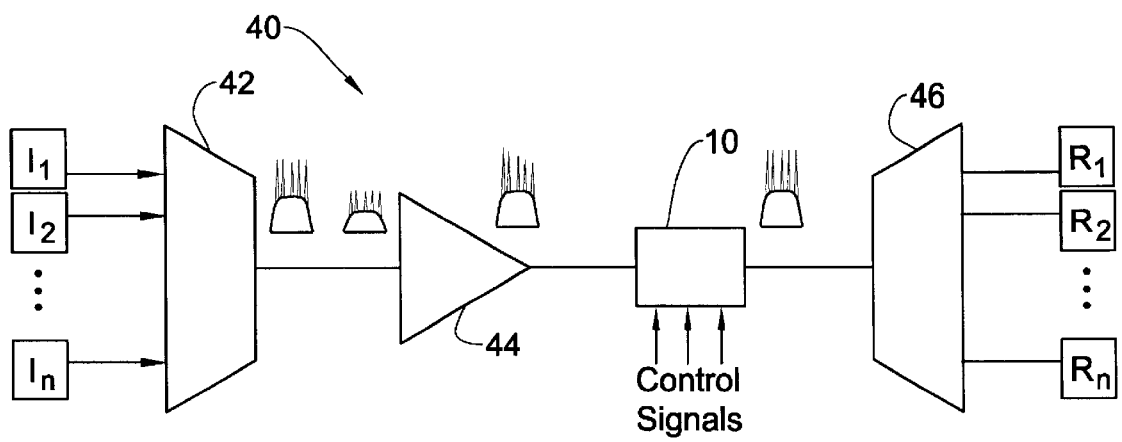
FIG. 11 illustrates how the device according to the invention can be used for correcting the wavelength-dependent distortions introduced by elements in optical communication systems.

Additionally, the device according to the invention can be used for correcting the wavelength-dependent distortions introduced by elements in optical communication systems. For example, by accommodating the device 10 upstream or downstream of an optical amplifier with wavelength dependent gain, or between two such amplifiers, the device can equalize the amplified power as a function of wavelength. This is illustrated in FIG. 11 showing a part of an optical communication system 40 composed of n transmitter units $I_1, I_2, \ldots, I_n$ with different center wavelengths, a multiplexer 42, an optical amplifier with wavelength selective gain 44, the electro-optical device 10, a demultiplexer 46, and n receiver units $R_1, R_2, \ldots, R_n$. In the present example, the electro-optical device 10 operates as an electrically-controlled equalizing filter.

Figure 12:
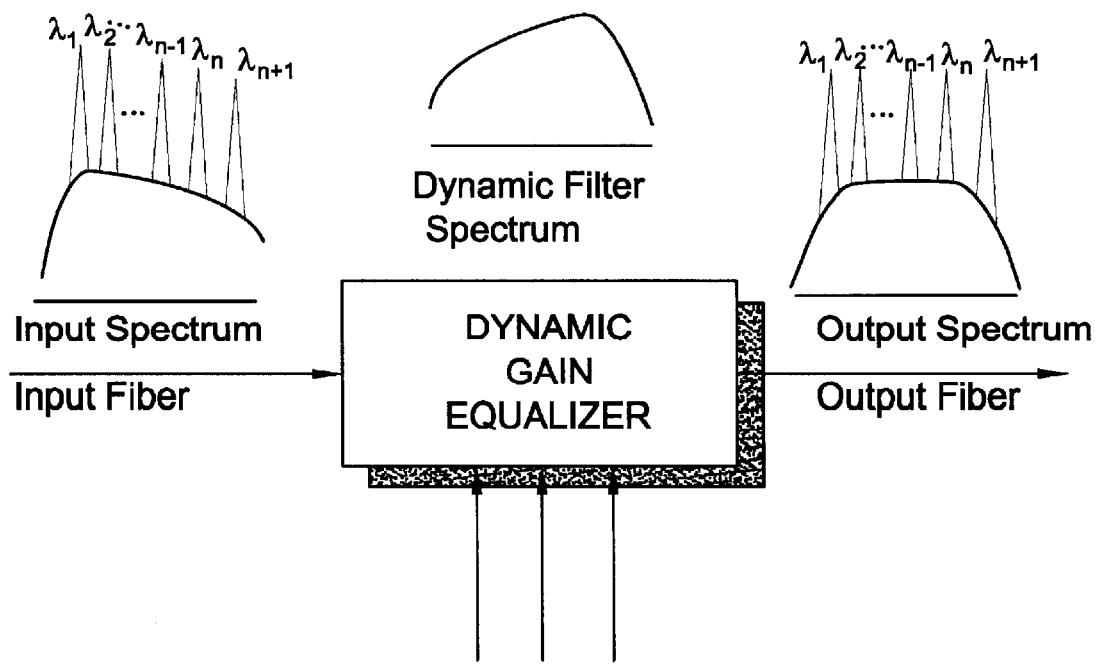
FIGS. 12 and 13 illustrate how the device of FIG. 1 can be used as a dynamic gain equalizer.
Figure 13:
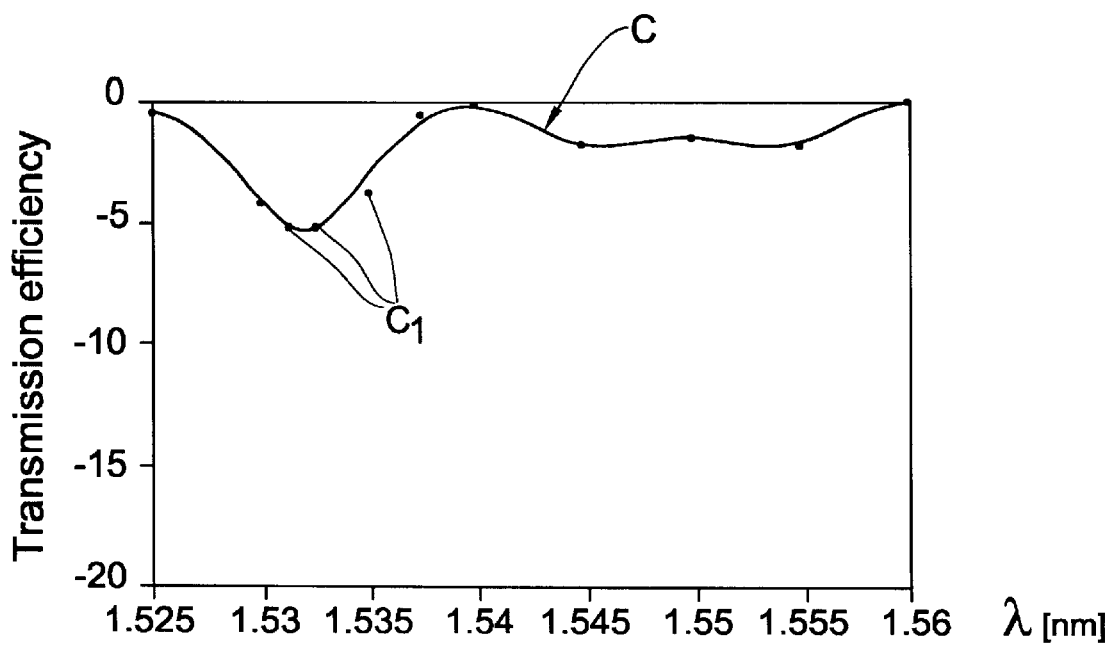

FIGS. 12 and 13 illustrate how the device 10 can be used as a dynamic gain equalizer. FIG. 13 shows the transmission as a function of wavelength (curve C) required for the gain equalization filter of an EDFA, as presented in the following article: IEEE Photonics Technology Papers 11, 536 (1999). A few points, generally at $C_1$, were taken from this graph to represent the required transmission. To create the appropriate transmission function, three gratings on a single periodically poled $LiNbO_3$ crystal were simulated, having the following parameters:

$\Lambda_1 \approx 10$ µm $d_1 \approx 5$ mm
$\Lambda_2 \approx 10.1$ µm $d_2 \approx 6$ mm
$\Lambda_3 \approx 10.15$ µm $d_3 \approx 6$ mm The angle of light propagation in the material is chosen to be ≈0.1047rad≈6°, the ratio between the voltages applied to the three gratings is 1:0.515:0.546, and the voltage of the first device is set to provide an attenuation of 5.4 dB at a wavelength of 1532 nm. The simulation results have shown that the filters according to the present invention can be used to generate the transmission function of FIG. 13. The remaining differences between the desired transmission and the one obtained with the three gratings are of the order of about 0.5 dB.

Thus, the present invention enables to use a domain-patterned ferroelectric crystal structure in an electro-optical device for controllable filtering and various wavelength selective optical systems. To achieve high spectral resolution of such a device, specific shaping of the beam and selection of appropriate angle of incidence can be used.

What is claimed is:

1. A method affecting the propagation of input light, the method comprising the steps of:
   (i) passing the input light through an electro-optical device composed of at least one domain-patterned ferroelectric crystal structure with inverted domains, and an electrodes' arrangement on the surface of the at least one structure connected to a voltage source; and
   (ii) applying voltage to the electrodes, thereby causing at least one of the following: deflecting a light component of a predetermined wavelengths contained in the input light from the direction of propagation of the input light so as to direct said light component in a reflection output direction, while allowing the other light components to propagate in said direction of propagation of the input light; changing the phase of the input light in a wavelength-dependent manner; and separately controlling the wavelength-dependent transmission and dispersion for different polarizations of light.

2. The method according to claim 1, wherein said input light is directed onto said electro-optical device at an angle substantially satisfying the Bragg condition, thereby selecting the light component of said predetermined wavelength from the input light.

3. A method affecting the propagation of input light formed of a plurality of light components of different wavelengths to select a light component of a predetermined wavelength from the input light, the method comprising:
   directing the input light onto an electro-optical device at an angle substantially satisfying the Bragg condition for said predetermined wavelength, wherein said electro-optical device is composed of a domain-patterned ferroelectric crystal structure with inverted domains, and an electrodes' arrangement on the surface of said structure connected to a power source; and
   applying voltage to the electrodes, thereby deflecting the light component of said predetermined wavelengths from the direction of propagation of the input light to propagate in a reflection output direction, while allowing the other wavelength components of the input light to propagate in said direction of propagation of the input light.

4. An electro-optical device comprising:
   (a) a domain-patterned ferroelectric crystal structure with inverted domains;

(b) an electrodes' arrangement on the surface of said structure connectable to a voltage source to selectively apply voltage to each of the electrodes;

(c) at least one input port for directing at least one input beam onto the structure; and (d) a control unit operating the voltage source to provide the desired voltage applied to the electrodes, and selectively operating said at least one input port to affect at least one of the following: an angle of incidence of the input beam onto the structure, a shape of the input beam, and propagation of light components of different polarizations contained in the input beam.

5. The device according to claim 4, wherein the crystal structure is fabricated from one of the following materials: $LiNbO_3$, $KTiOPO_4$, and $LiTaO_3$, $MgOLiNbO_3$, $KTiOAsO_4$, $RbTiOAsO_4$, $KNbO_3$.

6. The device according to claim 4, operable as a controllable filter.

7. The device according to claim 4, operable as a wavelength selective switch.

8. The device according to claim 7, wherein the wavelength selection is performed by directing the input beams onto said structure at different angles of incidence, thereby providing output beams ensuing from the structure with different angles of propagation, the angle of propagation of the output beam depending on the wavelength of the input beam.

9. The device according to claim 7, operable as an electrically-controlled drop switch.

10. The device according to claim 7, operable as an electrically-controlled add switch.

11. The device according to 8, operable as an add/drop switch.

12. The device according to claim 4, operable as a wavelength selective modulator.

13. The device according to claim 4, operable as an electrically-controlled dispersion element.

14. An optical communication system comprising an optical amplifier with wavelength dependent gain, and the electro-optical device constructed as defined in claim 4, the electro-optical device being operable for equalizing amplified power as a function of wavelength.

15. An optical communication system comprising the electro-optical device constructed as defined in claim 4, the system being capable of switching data packets formed of light of a specific wavelength.

16. The method according to claim 1, comprising the step of affecting a shape of the input beam propagating towards said structure so as to provide a substantially elliptical shape of the beam impinging onto the structure.

17. An electro-optical device comprising:

(a) a domain-patterned ferroelectric crystal structure with inverted domains;

(b) an electrodes' arrangement on the surface of said structure connectable to a voltage source to selectively apply voltage to each of the electrodes;

(c) an input port for directing an input beam onto the structure, said input port being operable to affect an angle of incidence of the input beam onto the structure so as to provide the input beam incidence onto the structure at an angle substantially satisfying the Bragg condition for a predetermined wavelength component of the input beam, and thereby cause deflection of said predetermined wavelength component from a direction of propagation of the input beam to a reflection output direction, while allowing propagation of the other wavelength components of the input beam in said direction of propagation of the input beam; and (d) a control unit operating the voltage source to apply voltage to the electrodes and operating said input port so as to provide the input beam incidence onto the structure at the angle substantially satisfying the Bragg condition for the predetermined wavelength component of the input beam.

18. An electro-optical device comprising:

(a) a domain-patterned ferroelectric crystal structure with inverted domains;

(b) an electrodes' arrangement on the surface of said structure connectable to a voltage source to selectively apply voltage to each of the electrodes;

(c) an input port for directing an input beam onto the structure, said input port being operable to affect a shape of the input beam so as to provide a substantially elliptical shape of the input beam impinging onto the structure; and (d) a control unit operating the voltage source to apply voltage to the electrodes and operating said input port so as to provide the substantially elliptical shape of the input beam.

* * * * *